United States Patent [19]

Mongelli et al.

[11] Patent Number: 5,596,105

[45] Date of Patent: Jan. 21, 1997

[54] THERAPEUTICALLY ACTIVE NAPHTHALENESULFONIC PYRROLECARBOXAMIDO DERIVATIVES

[75] Inventors: Nicola Mongelli, Milan; Giovanni Biasoli, Gavirate; Maria Grandi, Reggio Emilia; Marina Ciomei, Torre d'Isola; Maria C. Geroni, Milan, all of Italy

[73] Assignee: Farmitalia Carlo Erba S.r.L., Milan, Italy

[21] Appl. No.: 372,872

[22] Filed: Jan. 13, 1995

Related U.S. Application Data

[63] Continuation of Ser. No. 97,015, Jul. 27, 1993, abandoned.

[30] Foreign Application Priority Data

Aug. 11, 1992 [GB] United Kingdom .................. 9216962

[51] Int. Cl.$^6$ .................................................. C07D 207/36
[52] U.S. Cl. .................................................. 548/518; 548/537
[58] Field of Search .................................. 548/518, 537; 514/422, 423

[56] References Cited

U.S. PATENT DOCUMENTS

| | | | |
|---|---|---|---|
| 4,112,076 | 9/1978 | Arcamone et al. | 424/180 |
| 4,133,877 | 1/1979 | Masi et al. | 424/180 |
| 4,134,903 | 1/1979 | Masi et al. | 260/365 |
| 4,166,848 | 9/1979 | Bernardi et al. | 424/180 |
| 4,188,377 | 2/1980 | Suarato et al. | 424/180 |
| 4,191,755 | 3/1980 | Masi et al. | 424/180 |
| 4,191,756 | 3/1980 | Masi et al. | 424/180 |
| 4,265,885 | 5/1981 | Bargiotti et al. | 424/180 |
| 4,267,116 | 5/1981 | Masi et al. | 260/376 |
| 4,268,451 | 5/1981 | Masi et al. | 260/376 |
| 4,325,946 | 4/1982 | Bargiotti et al. | 424/180 |
| 4,327,029 | 4/1982 | Bernardi et al. | 260/351.1 |
| 4,345,068 | 8/1982 | Suarato et al. | 536/17 A |
| 4,345,070 | 8/1982 | Suarato et al. | 536/17 A |
| 4,366,149 | 12/1982 | Bargiotti et al. | 424/180 |
| 4,393,052 | 7/1983 | Bargiotti et al. | 424/180 |
| 4,438,105 | 3/1984 | Suarato et al. | 424/180 |
| 4,522,815 | 6/1985 | Bargiotti et al. | 514/34 |
| 4,672,057 | 6/1987 | Bargiotti et al. | 514/34 |
| 4,684,629 | 8/1987 | Bargiotti et al. | 514/34 |
| 4,839,346 | 6/1989 | Bargiotti et al. | 514/34 |
| 4,912,199 | 3/1990 | Lown et al. | 530/331 |
| 4,965,351 | 10/1990 | Caruso et al. | 536/6.4 |
| 4,985,548 | 1/1991 | Caruso et al. | 536/6.4 |
| 4,987,126 | 1/1991 | Bargiotti et al. | 514/34 |
| 5,045,534 | 9/1991 | Bargiotti et al. | 514/34 |
| 5,260,329 | 11/1993 | Mongelli et al. | 514/422 |
| 5,304,687 | 4/1994 | Bargiotti et al. | 568/604 |
| 5,332,756 | 7/1994 | Mongelli et al. | 514/459 |

FOREIGN PATENT DOCUMENTS

| | | |
|---|---|---|
| 0183582 | 6/1986 | European Pat. Off. . |
| 0183352 | 6/1986 | European Pat. Off. . |
| 0486809 | 5/1992 | European Pat. Off. . |
| 2261661 | 5/1993 | United Kingdom . |
| WO91/10649 | 7/1991 | WIPO . |
| WO92/13838 | 8/1992 | WIPO . |

OTHER PUBLICATIONS

Biology, 5th Edition, Worth Publishers, New York, New York, 1989, pp. 449–450.

Poli et al, "The Effect of Cytokines and Pharmacologic Agents on Chronic HIV Infection", AIDS Research and Human Retroviruses, vol. 8, No. 2, (1992), pp. 191–197.

Lau et al, "The Role of Interferon and Tumor Necrosis Factor in the Pathogenesis of AIDS", Journal of Experimental Pathology, vol. 5, No. 3, (1990), pp. 111–122.

J. Med. Chem., 1989, 32, pp. 2368–2375, J. W. Lown, et al., "Novel Linked Antiviral and Anti–Tumor Agents Related to Netropsin and Distamycin: Synthesis and Biological Evaluation".

*Primary Examiner*—S. Mark Clardy
*Assistant Examiner*—B. Bembenick
*Attorney, Agent, or Firm*—Oblon, Spivak, McClelland, Maier & Neustadt, P.C.

[57] ABSTRACT

The invention relates to naphthalenesulfonic-pyrrolecarboxamido compounds of formula

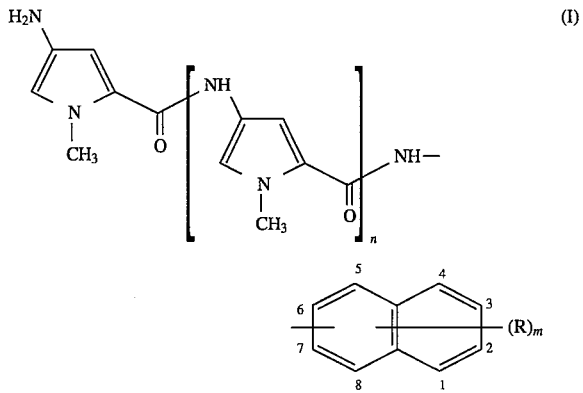

wherein n is zero or an integer of 1 to 3; R is a sulfonic acid residue; m is an integer of 1 to 3, or a pharmaceutically acceptable salt thereof, which are active as antiviral agents, in particular against Human Immunodeficiency Virus

2 Claims, No Drawings

THERAPEUTICALLY ACTIVE NAPHTHALENESULFONIC PYRROLECARBOXAMIDO DERIVATIVES

This application is a continuation of U.S. Ser. No. 08/097,015 filed Jul. 27, 1993 now abandoned.

The present invention relates to naphthalenesulfonic-pyrrolecarboxamido compounds having therapeutic utility as antiviral agents, in particular as anti-HIV agents.

WO 91/10649 provides ureido derivatives of poly-4-amino-2-carboxy-1-methyl compounds which have angiogenesis inhibitor activity and have TNF-α neutralizing activity.

Accordingly, these prior art compounds can be useful in treating several pathological conditions in mammals where the growth of new blood vessels is detrimental and in which TNF-α is known to play a detrimental role.

Now we have found that intermediate compounds previously disclosed in the above mentioned international application are endowed with therapeutically useful properties, in particular with antiviral activity against Human Immunodeficiency Virus (HIV).

Accordingly, the present invention provides naphthalenesulfonic-pyrrolecarboxamido derivatives having the general formula (I)

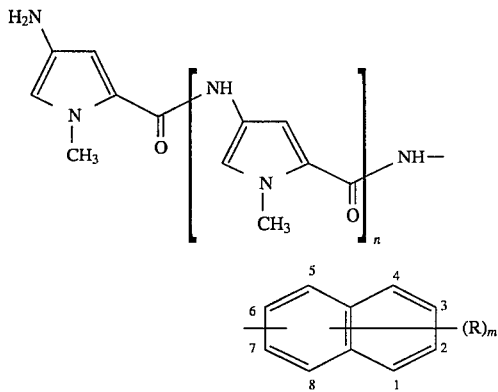

wherein n is zero or an integer of 1 to 3; R is a sulfonic acid residue; m is an integer of 1 to 3; or a pharmaceutically acceptable salt thereof, for use as an active therapeutic substance.

The substituted naphthyl group is preferably a 5-, 6-7- or 8-naphthyl group, typically a 7- or 8-naphthyl group. When m is 3 in formula (I) so that the naphthyl group is substituted by three sulfonic acid groups, the sulfonic acid substituents are preferably in the 1-, 3- and 5- or 1-, 3- and 6-positions. When m is 2, the sulfonic acid substituents are preferably in the 1- and 3-, 1- and 5-, 3- and 5- or 3- and 6-positions. When m is 1, the sulfonic acid substituent is preferably in the 1-, 3- or 5-position.

The invention also includes within its scope all the possible isomers, stereoisomers and their mixtures and the metabolites and the metabolic precursors or bio-precursors of the compounds of formula (I).

As already said, the invention includes within its scope also the pharmaceutically acceptable salts of the compounds of formula (I).

Examples of pharmaceutically acceptable salts are either those with inorganic bases, such as sodium, potassium, calcium and aluminium hydroxides, or with organic bases, such as lysine, arginine, N-methylglucamine, triethylamine, triethanolamine, dibenzylamine, methylbenzylamine, di-(2-ethyl-hexyl)-amine piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines.

As stated above the present invention also includes within its scope pharmaceutically acceptable bio-precursors (otherwise known as pro-drugs) of the compounds of formula (I), i.e. compounds which have a different formula to formula (I) above but which nevertheless upon administration to a human being are converted directly or indirectly in vivo into a compound of formula (I). Specific examples of compounds of formula (I) are the following, especially in the form of sulfonic acid sodium salt, either as free bases or as hydrochlorides:

8-(Amino-N-methyl-4,2-pyrrolecarbonylimino) (1,3,5-naphthalentrisulfonic acid);
7-(Amino-N-methyl -4,2-pyrrolecarbonylimino) (1,3,5-naphthalentrisulfonic acid);
6-(Amino-N-methyl-4,2-pyrrolecarbonylimino) (1,3,5-naphthalentrisulfonic acid);
8-(Amino-N-methyl-4,2-pyrrolecarbonylimino) (1,3,6-naphthalentrisulfonic acid);
7-(Amino-N-methyl-4,2-pyrrolecarbonylimino) (1,3,6-naphthalentrisulfonic acid);
8-(Amino-N-methyl-4,2-pyrrolecarbonylimino) (1,3-naphthalendisulfonic acid);
7-(Amino-N-methyl-4,2-pyrrolecarbonylimino) (1,3,-naphthalendisulfonic acid);
6-(Amino-N-methyl-4,2-pyrrolecarbonylimino)(1,3-naphthalendisulfonic acid);
5-(Amino-N-methyl-4,2-pyrrolecarbonylimino)(1,3-naphthalendisulfonic acid);
8-(Amino-N-methyl-4,2-pyrrolecarbonylimino)(1,5-naphthalendisulfonic acid);
7-(Amino-N-methyl-4,2-pyrrolecarbonylimino)(1,5-naphthalendisulfonic acid);
6-(Amino-N-methyl-4,2-pyrrolecarbonylimino)(1,5-naphthalendisulfonic acid);
8-(Amino-N-methyl-4,2-pyrrolecarbonylimino)(3,5-naphthalendisulfonic acid);
7-(Amino-N-methyl-4,2-pyrrolecarbonylimino)(3,5-naphthalendisulfonic acid);
6-(Amino-N-methyl-4,2-pyrrolecarbonylimino)(3,5-naphthalendisulfonic acid);
8-(Amino-N-methyl-4,2-pyrrolecarbonylimino)(3,6-naphthalendisulfonic acid);
7-(Amino-N-methyl-4,2-pyrrolecarbonylimino)(3,6-naphthalendisulfonic acid);
8-(Amino-N-methyl-4,2-pyrrolecarbonylimino)(1-naphthalensulfonic acid);
7-(Amino-N-methyl-4,2-pyrrolecarbonylimino) (1-naphthalensulfonic acid);
8-(Amino-N-methyl-4,2-pyrrolecarbonylimino) (3-naphthalensulfonic acid);
7-(Amino-N-methyl-4,2-pyrrolecarbonylimino) (3-naphthalensulfonic acid);
8-(Amino-N-methyl-4,2-pyrrolecarbonylimino) (5-naphthalensulfonic acid);
7-(Amino-N-methyl-4,2-pyrrolecarbonylimino) (5-naphthalensulfonic acid);
8-(Amino-N-methyl-4,2-pyrrolecarbonyl-imino(N-methyl-4,2-pyrrole)carbonylimino) (1,3,5-naphthalentrisulfonic acid);
7-(Amino-N-methyl-4,2-pyrrolecarbonyl-imino(N-methyl-4,2-pyrrole)carbonylimino) (1,3,5-naphthalentrisulfonic acid);
6-(Amino-N-methyl-4,2-pyrrolocarbonyl-imino(N-methyl-4,2-pyrrole)carbonylimino) (1,3,5-naphthalentrisulfonic acid);

8-(Amino-N-methyl-4,2-pyrrolecarbonyl-imino(N-methyl-4,2-pyrrole)carbonylimino) (1,3,6-naphthalentrisulfonic acid);

7-(Amino-N-methyl-4,2-pyrrolecarbonyl-imino(N-methyl-4,2-pyrrole)carbonylimino) (1,3,6-naphthalentrisulfonic acid);

8-(Amino-N-methyl-4,2-pyrrolecarbonyl-imino(N-methyl-4,2-pyrrole)carbonylimino) (1,3-naphthalendisulfonic acid);

7-(Amino-N-methyl-4,2-pyrrolecarbonyl-imino(N-methyl-4,2-pyrrole)carbonylimino) (1,3-naphthalendisulfonic acid);

6-(Amino-N-methyl-4,2-pyrrolecarbonyl-imino(N-methyl-4,2-pyrrole)carbonylimino) (1,3-naphthalendisulfonic acid);

5-(Amino-N-methyl-4,2-pyrrolecarbonyl-imino(N-methyl-4,2-pyrrole)carbonylimino) (1,3-naphthalendisulfonic acid);

8-(Amino-N-methyl-4,2-pyrrolecarbonyl-imino(N-methyl-4,2-pyrrole)carbonylimino) (1,5-naphthalendisulfonic acid);

7-(Amino-N-methyl-4,2-pyrrolecarbonyl-imino(N-methyl-4,2-pyrrole)carbonylimino) (1,5-naphthalendisulfonic acid);

6-(Amino-N-methyl-4,2-pyrrolecarbonyl-imino(N-methyl-4,2-pyrrole)carbonylimino) (1,5-naphthalendisulfonic acid);

8-(Amino-N-methyl-4,2-pyrrolecarbonyl-imino(N-methyl-4,2-pyrrole)carbonylimino) (3,5-naphthalendisulfonic acid);

7-(Amino-N-methyl-4,2-pyrrolecarbonyl-imino(N-methyl-4,2-pyrrole)carbonylimino) (3,5-naphthalendisulfonic acid);

6-(Amino-N-methyl-4,2-pyrrolecarbonyl-imino(N-methyl-4,2-pyrrole)carbonylimino) (3,5-naphthalendisulfonic acid);

8-(Amino-N-methyl-4,2-pyrrolecarbonyl-imino(N-methyl-4,2-pyrrole)carbonylimino) (3,6-naphthalendisulfonic acid);

7-(Amino-N-methyl-4,2-pyrrolecarbonyl-imino(N-methyl-4,2-pyrrole)carbonylimino) (3,6-naphthalendisulfonic acid);

8-(Amino-N-methyl-4,2-pyrrolecarbonyl-imino(N-methyl-4,2-pyrrole)carbonylimino) (1-naphthalensulfonic acid);

7-(Amino-N-methyl-4,2-pyrrolecarbonyl-imino(N-methyl-4,2-pyrrole)carbonylimino) (1-naphthalensulfonic acid);

8-(Amino-N-methyl-4,2-pyrrolecarbonyl-imino(N-methyl-4,2-pyrrole)carbonylimino)(3-naphthalensulfonic acid);

7-(Amino-N-methyl-4,2-pyrrolecarbonyl-imino(N-methyl-4,2-pyrrole)carbonylimino)(3-naphthalensulfonic acid);

8-(Amino-N-methyl-4,2-pyrrolecarbonyl-imino(N-methyl-4,2-pyrrole)carbonylimino)(5-naphthalensulfonic acid);

7-(Amino-N-methyl-4,2-pyrrolecarbonyl-imino(N-methyl-4,2-pyrrole)carbonylimino)(5-naphthalensulfonic acid);

8-(Amino-N-methyl-4,2-pyrrolecarbonyl-imino(N-methyl-4,2-pyrrole)carbonyl-imino)(N-methyl-4,2-pyrrole)carbonylimino)(1,3,5-naphthalentrisulfonic acid);

7-(Amino-N-methyl-4,2-pyrrolecarbonyl-imino(N-methyl-4,2-pyrrole)carbonyl-imino(N-methyl-4,2-pyrrole)carbonylimino)(1,3,5-naphthalentrisulfonic acid);

6-(Amino-N-methyl-4,2-pyrrolecarbonyl-imino(N-methyl-4,2-pyrrole)carbonyl-imino-(N-methyl-4,2-pyrrole)carbonylimino)(1,3,5-naphthalentrisulfonic acid);

8-(Amino-N-methyl-4,2-pyrrolecarbonyl-imino(N-methyl-4,2-pyrrole)carbonyl-imino(N-methyl-4,2-pyrrole)carbonylimino)(1,3,6-naphthalentrisulfonic acid);

7-(Amino-N-methyl-4,2-pyrrolecarbonyl-imino(N-methyl-4,2-pyrrole)carbonyl-imino(N-methyl-4,2-pyrrole)carbonylimino)(1,3,6-naphthalentrisulfonic acid);

8-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);

7-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);

6-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);

5-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);

8-(Amino-N-methyl-4,2-pyrrolecarbonyl-imino (N-methyl-4,2-pyrrole)carbonyl-imino(N-methyl-4,2-pyrrole)carbonylimino)(1,5-naphthalendisulfonic acid);

7-(Amino-N-methyl-4,2-pyrrolecarbonyl-imino(N-methyl-4,2-pyrrole)carbonyl-imino(N-methyl-4,2-pyrrole)carbonylimino)(1,5-naphthalendisulfonic acid);

6-(Amino-N-methyl-4,2-pyrrolecarbonyl-imino(N-methyl-4,2-pyrrole)carbonyl-imino(N-methyl-4,2-pyrrole)carbonylimino)(1,5-naphthalendisulfonic acid);

8-(Amino-N-methyl-4,2-pyrrolecarbonyl-imino(N-methyl-4,2-pyrrole)carbonyl-imino(N-methyl-4,2-pyrrole)carbonylimino)(3,5-naphthalendisulfonic acid);

7-(Amino-N-methyl-4,2-pyrrolecarbonyl-imino(N-methyl-4,2-pyrrole)carbonyl-imino(N-methyl-4,2-pyrrole)carbonylimino)(3,5-naphthalendisulfonic acid);

6-(Amino-N-methyl-4,2-pyrrolecarbonyl-imino(N-methyl-4,2-pyrrole)carbonyl-imino(N-methyl-4,2-pyrrole)carbonylimino)(3,5-naphthalendisulfonic acid);

8-(Amino-N-methyl-4,2-pyrrolecarbonyl-imino(N-methyl-4,2-pyrrole)carbonyl-imino(N-methyl-4,2-pyrrole)carbonylimino)(3,6-naphthalendisulfonic acid);

7-(Amino-N-methyl-4,2-pyrrolecarbonyl-imino(N-methyl-4,2-pyrrole)carbonyl-imino(N-methyl-4,2-pyrrole)carbonylimino)(3,6-naphthalendisulfonic acid);

8-(Amino-N-methyl-4,2-pyrrolecarbonyl-imino(N-methyl-4,2-pyrrole)carbonyl-imino(N-methyl-4,2-pyrrole)carbonylimino)(1-naphthalensulfonic acid);

7-(Amino-N-methyl-4,2-pyrrolecarbonyl-imino(N-methyl-4,2-pyrrole)carbonyl-imino(N-methyl-4,2-pyrrole)carbonylimino)(1-naphthalensulfonic acid);

8-(Amino-N-methyl-4,2-pyrrolecarbonyl-imino(N-methyl-4,2-pyrrole)carbonyl-imino(N-methyl-4,2-pyrrole)carbonylimino)(3-naphthalensulfonic acid);

7-(Amino-N-methyl-4,2-pyrrolecarbonyl-imino(N-methyl-4,2-pyrrole)carbonyl-imino(N-methyl-4,2-pyrrole)carbonylimino)(3-naphthalensulfonic acid);

8-(Amino-N-methyl-4,2-pyrrolecarbonyl-imino(N-methyl-4,2-pyrrole)carbonyl-imino(N-methyl-4,2-pyrrole)carbonylimino)(5-naphthalensulfonic acid);

7-(Amino-N-methyl-4,2-pyrrolecarbonyl-imino(N-methyl-4,2-pyrrole)carbonyl-imino(N-methyl-4,2-pyrrole)carbonylimino)(5-naphthalensulfonic acid);

8-(Amino-N-methyl-4,2-pyrrolecarbonyl-imino-(N-methyl-4,2-pyrrole)carbonyl-imino(N-methyl-4,2-pyrrole ) carbonyl-imino(N-methyl-4,2-pyrrole)carbonylimino(1,3,5-naphthalentrisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino(1,3,5-naphthalentrisulfonic acid);

6-(Amino-N-methyl-4,2-pyrrolecarbonyl-imino-(N-methyl-4,2-pyrrole)carbonyl-imino(N-methyl-4,2-pyrrole)carbonylimino(1,3,5-naphthalentrisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino(1,3,6-naphthalentrisulfonic acid);

7-(Amino-N -methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3,6-naphthalentrisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3-naphthalendisulfonic acid);

6-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3-naphthalendisulfonic acid);

5-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,5-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,5-naphthalendisulfonic acid);

6-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,5-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,5-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,5-naphthalendisulfonic acid);

6-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,5-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,6-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,6-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino(1-naphthalensulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1-naphthalensulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole) carbonylimino (3-naphthalensulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3-naphthalensulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino (N-methyl-4,2-pyrrole)carbonylimino (5-naphthalensulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino (N-methyl-4,2-pyrrole)carbonylimino (5-naphthalensulfonic acid), and the pharmaceutically acceptable salts thereof.

A further object of the present invention is to provide a pharmaceutical composition comprising a pharmaceutically acceptable carrier and/or diluent and, as an active agent, a compound of formula (I), as defined above, or a pharmaceutically acceptable salt thereof.

The present invention also provides the use of a compound of formula (I), as defined above, or a pharmaceutically acceptable salt thereof, in the preparation of a pharmaceutical composition for use as antiviral agent, in particular against HIV.

Object of the present invention are also products containing a compound of formula (I), or a pharmaceutically acceptable salt thereof, and a different biologically active agent, as a combined preparation for simultaneous, separate or sequential use in the treatment of a viral disease, in particular against HIV.

The present invention also provides a combined method of treatment of a viral disease, in particular against HIV. The term "combined" method of treatment is meant to include both separate and substantially contemporaneous administration of a composition containing a compound of formula (I), or a pharmaceutically acceptable salt thereof, and a pharmaceutical composition containing a different pharmaceutically active agent.

Active agents, that can be formulated with a compound of the invention or, alternatively, can be administered in a combined method of treatment depend on the disease state to be cured and are, for instance, drugs that affect the pathogenesis of HIV-induced diseases.

For example the compounds of the invention may be employed with various active agents, in particular those that affect reverse transcriptase, antimicrobial and antitumor agents or a mixture of two or more thereof.

Drugs of interest include non-nucleoside reverse transcriptase inhibitors e.g. nevirapine; nucleoside derivatives e.g. zidovudine and didanosine; acyclovir; ribavirin; ascorbic acid; protease inhibitors; cytokines e.g. IL-1, IL-2, IL-3 or IL-4; growth factors; interferons e.g. alpha- or gamma interferon; antitumor agents, e.g. doxorubicin, daunomycin, epirubicin, idarubicin, etoposide, fluorouracil, mephalan, cyclophosphamide, bleomycin, vinblastin and mitomycin; immuno-modulating agents, in particular immunostimulants, gamma globulin, immune globulin and monoclonal antibody products, antibiotics and antimicrobial products.

Typically, the antimicrobial agents may include a penicillin in conjunction with an aminoglycoside (e.g. gentamycin, tobramycin).

However several well known additional agents, e.g. cephalosporins, can be utilized.

As stated above the compounds of the invention have been found to be active as antiviral agents, in particular against Human Immunodeficiency Virus (HIV). The compounds are therefore useful in treating an infection attributable to a RNA virus, especially a retrovirus. The retrovirus may be HIV-1 or HIV-2. For instance, the compounds of formula (I) have been found active in the biological test described in J. Natl. Cancer Inst. 81: 577–586, 1989 and therefore can be used in treating AIDS. A compound of the invention can therefore be used to improve the condition of a patient suffering from AIDS.

In particular the compounds of the invention can be used in the preparation of an agent to be used in the treatment of a human patient who is seropositive diseased, stressed or pathological as a result of infection with a RNA virus, in particular HIV, or who is suffering from induced disease e.g. lymphadenopathy syndrome (LS), AIDS-related complex (ARC), AIDS or Kaposi's sarcoma. The condition of a human patient can thus be ameliorated or improved.

The compounds of the invention can be administered by the usual routes, for example, parenterally, e.g. by intravenous injection or infusion, intramuscularly, subcutaneously, topically or orally. The dosage depends on the age, weight and condition of the patient and on the administration route. For example, a suitable dosage for administration to adult humans of the compound 8-(amino-N-methyl-4,2-pyrrole-carbonyl-imino-(N-methyl-4,2-pyrrole)carbonylimino)(1,3,5-naphthalentrisulfonic acid) may range from about 0.5 to about 300 mg per dose 1–4 times a day. The pharmaceutical compositions of the invention may contain a compound of formula (I) as the active substance, in association with one or more pharmaceutically acceptable excipients and/or carrier.

The pharmaceutical compositions of the invention are usually prepared following conventional methods and are administered in a pharmaceutically suitable form.

For instance, solutions for intravenous injection or infusion may contain as carrier, for example, sterile water or preferably, they may be in the form of sterile aqueous isotonic saline solutions. Suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleoginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates: and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes. The compounds of formula (I) and the salts thereof can be obtained according to known procedures. For instance, as disclosed in WO 91/10649, a compound of formula (I) can be obtained by reduction of a compound of formula (II), or a salt thereof.

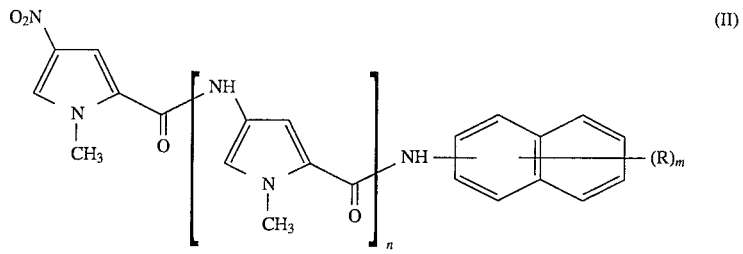

wherein

R, m and n are as defined above by methods well known in the art for the reduction of a nitro group into an amino group. The reduction is typically achieved by catalytic hydrogenation with Pd/C, Pt or Rh in a protic solvent such as water, a lower alkanol such as a $C_1$–$C_4$ alkanol and preferably methanol or ethanol, or a mixture of such protic solvents, under a pressure from about 15 p.s.i. to about 150 p.s.i. The reduction may also be achieved by chemical reduction, for example with Fe/mineral acid such as HCl or $H_2SO_4$, at a temperature from about room temperature to about 90° C., for example to about 30° C. A salt of a compound of formula (II) may be a salt with inorganic bases, for example those mentioned above as to the pharmaceutically acceptable salts of the invention, the sodium and potassium salts being the preferred.

The compounds of formula (II) can be obtained by reacting an amine of formula B-$NH_2$, where B is a naphthyl group substituted by 1 to 3 sulfonic residues, with a compound of formula (III)

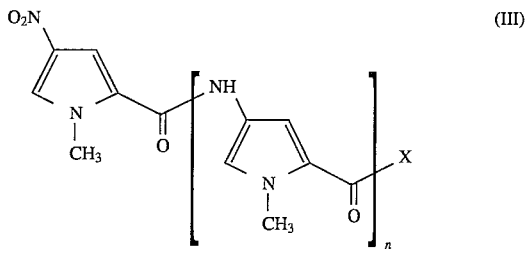

wherein

X is an appropriate leaving group, for instance a halogen atom, in particular chlorine or another easily displaceable group such as imidazolyl, triazolyl, p-nitrophenoxy, trichlorophenoxy or trichloromethyloxy.

Also, the reaction of an amine of formula B-$NH_2$ with a compound of formula (III) is a well known process. The reaction can be carried out for instance in water, in the presence of a basic agent such as NaOH, KOH, $CH_3COONa$ or mixtures thereof as acid acceptor at a temperature from about 0° C. to about 35° C. Alternatively the reaction can be carried out in an inert organic solvent, for example diethyl ether, benzene, methylene chloride, chloroform or dioxane, in the presence of a tertiary organic base e.g. triethylamine as acid acceptor, at a temperature from about −10° C. to about 70° C. Alternatively a compound of formula (II) wherein n is 1, 2 or 3, may be obtained by a multi-step-process comprising reacting a compound of formula (IV):

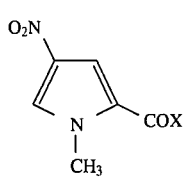

wherein
X is as defined above, with an amine of formula B-NH$_2$, in which B is as defined above. The reaction, which may be carried out according to known methods for example as described for the reaction between the compound of formula (III) and amine B-NH$_2$, provides compounds of formula (V):

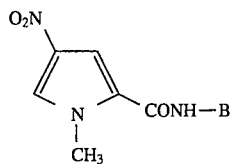

wherein
B is as defined above.

A compound of formula (V) is reduced according to known methods, for example as described for the reduction of the compound of formula (II), to provide a compound of formula (VI):

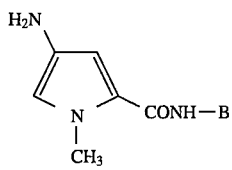

wherein
B is as defined above, which in its turn is reacted according to the same methods herein described with a compound of formula (IV), as defined above, thus obtaining a compound of formula (II), as defined above, wherein n is 1.

If a compound of formula (II) wherein n in 2 or 3 is desired, one or two further reduction and acylation steps are required.

The compounds of formula (III) are known compounds and may be obtained for example according to Heterocycles, vol. 237, No. 8, 1988, pp. 1945–52.

The compounds of formula (IV) and the amine of formula B—NH$_2$ are known products or may be easily obtained according to known methods.

The compounds of formula (II) for use as therapeutic agents, particularly as antiviral agents, especially against the HIV virus, constitute a further object of the present invention.

Moreover the compounds of formula (I) and the compounds of formula (II) wherein n is 3 and their pharmaceutically acceptable salts are novel compounds and as such they represent an object of the present invention too. A compound of formula (I) wherein n is 3 or a pharmaceutically acceptable salt thereof is prepared by a process which comprises reducing a compound of formula (II) or a salt thereof:

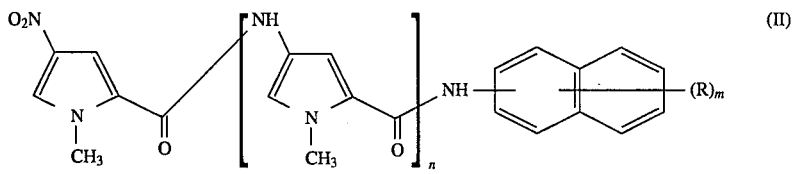

wherein R and m are as defined above and n is 3 and, if desired, converting the resulting compound of formula (I) into a pharmaceutically acceptable salt thereof. The following-Examples-illustrate but do not limit the invention.

EXAMPLE 1

8-(Amino-N-methyl-4,2-pyrrolecarbonyl-imino(N-methyl-4,2-pyrrole)carbonylimino))(1,3,5-naphthalentrisulfonic acid trisodium salt), hydrochloride.

The compound 8-(nitro-N-methyl-4,2-pyrrolecarbonyl-imino(N-methyl-4,2-pyrrole)carbonylimino))(1,3,5-naphthalentrisulfonic acid trisodium salt) (2.17 g=3 mmol) was dissolved into a mixture of water (120 ml) and 1N HCl (3 ml) and reduced over a Pd catalyst
(10% on carbon; mg 900) under H$_2$ pressure (50 p.s.i.) for 3 hours. The catalyst was filtered and the resulting solution was concentrated in vacuum to dryness, affording 2,1 g of the title compound.

I.R. (KBr) cm$^{-1}$: 3440 b, 1640, 1520, 1190, 1030. N.M.R. (DMSO-d6): 3.85 (3H,s); 3.90 (3H,s); 7.1 (3H,m); 7.4 (1H,d); 7.95 (2H,m); 8.60 (1H,d); 9.35 (1H,d); 10.1 (4H,bs); 12.3 (1H,bs)

By proceeding analogously the following compounds can be prepared as sulfonic acid sodium salts, and hydrochlorides:

8-(Amino-N-methyl-4,2-pyrrolecarbonylimino)(1,3,5-naphthalentrisulfonic acid);
7-(Amino-N-methyl-4,2-pyrrolecarbonylimino)(1,3,5-naphthalentrisulfonic acid);
6-(Amino-N-methyl-4,2-pyrrolecarbonylimino)(1,3,5-naphthalentrisulfonic acid);
8-(Amino-N-methyl-4,2-pyrrolecarbonylimino)(1,3,6-naphthalentrisulfonic acid);
7-(Amino-N-methyl-4,2-pyrrolecarbonylimino)(1,3,6-naphthalentrisulfonic acid);
8-(Amino-N-methyl-4,2-pyrrolecarbonylimino)(1,3-naphthalendisulfonic acid);
7-(Amino-N-methyl-4,2-pyrrolecarbonylimino)(1,3-naphthalendisulfonic acid);
6-(Amino-N-methyl-4,2-pyrrolecarbonylimino)(1,3-naphthalendisulfonic acid);
5-(Amino-N-methyl-4,2-pyrrolecarbonylimino)(1,3-naphthalendisulfonic acid);
8-(Amino-N-methyl-4,2-pyrrolecarbonylimino)(1,5-naphthalendisulfonic acid);
7-(Amino-N-methyl-4,2-pyrrolecarbonylimino)(1,5-naphthalendisulfonic acid);
6-(Amino-N-methyl-4,2-pyrrolecarbonylimino)(1,5-naphthalendisulfonic acid);
8-(Amino-N-methyl-4,2-pyrrolecarbonylimino)(3,5-naphthalendisulfonic acid);
7-(Amino-N-methyl-4,2-pyrrolecarbonylimino) (3,5-naphthalendisulfonic acid);
6-(Amino-N-methyl-4,2-pyrrolecarbonylimino) (3,5-naphthalendisulfonic acid);
8-(Amino-N-methyl-4,2-pyrrolecarbonylimino) (3,6-naphthalendisulfonic acid);
7-(Amino-N-methyl-4,2-pyrrolecarbonylimino) (3,6-naphthalendisulfonic acid);

8-(Amino-N-methyl-4,2-pyrrolecarbonylimino)(1-naphthalensulfonic acid);

7-(Amino-N-methyl-4,2-pyrrolecarbonylimino)(1-naphthalensulfonic acid);
8-(Amino-N-methyl-4,2-pyrrolecarbonylimino)(3-naphthalensulfonic acid);
7-(Amino-N-methyl-4,2-pyrrolecarbonylimino)(3-naphthalensulfonic acid);
8-(Amino-N-methyl-4,2-pyrrolecarbonylimino)(5-naphthalensulfonic acid);
7-(Amino-N-methyl-4,2-pyrrolecarbonylimino)(5-naphthalensulfonic acid);
7- (Amino-N-methyl-4,2-pyrrolecarbonyl-imino(N-methyl-4,2-pyrrole)carbonylimino)(1,3,5-naphthalentrisulfonic acid);
6- (Amino-N-methyl-4,2-pyrrolocarbonyl-imino(N-methyl-4,2-pyrrole)carbonylimino)(1,3,5-naphthalentrisulfonic acid);
8- (Amino-N-methyl-4,2-pyrrolecarbonyl-imino(N-methyl-4,2-pyrrole)carbonylimino)(1,3,6-naphthalentrisulfonic acid);
7-(Amino-N-methyl-4,2-pyrrolecarbonyl-imino(N-methyl-4,2-pyrrole)carbonylimino)(1,3,6-naphthalentrisulfonic acid);
8-(Amino-N-methyl-4,2-pyrrolecarbonyl-imino(N-methyl-4,2-pyrrole)carbonylimino)(1,3-naphthalendisulfonic acid);
7-(Amino-N-methyl-4,2-pyrrolecarbonyl-imino(N-methyl-4,2-pyrrole)carbonylimino)(1,3-naphthalendisulfonic acid);
6-(Amino-N-methyl-4,2-pyrrolecarbonyl-imino(N-methyl-4,2-pyrrole)carbonylimino)(1,3-naphthalendisulfonic acid);
5-(Amino-N-methyl-4,2-pyrrolecarbonyl-imino(N-methyl-4,2-pyrrole)carbonylimino)(1,3-naphthalendisulfonic acid);
8-(Amino-N-methyl-4,2-pyrrolecarbonyl-imino(N-methyl-4,2-pyrrole)carbonylimino)(1,5 -naphthalendisulfonic acid);
7-(Amino-N-methyl- 4,2-pyrrolecarbonyl-imino(N-methyl-4,2-pyrrole)carbonylimino)(1,5-naphthalendisulfonic acid);
6-(Amino-N-methyl-4,2-pyrrolecarbonyl-imino(N-methyl-4,2-pyrrole)carbonylimino)(1,5-naphthalendisulfonic acid);
8-(Amino-N-methyl-4,2-pyrrolecarbonyl-imino(N-methyl-4,2-pyrrole)carbonylimino)(3,5-naphthalendisulfonic acid);
7-(Amino-N-methyl-4,2-pyrrolecarbonyl-imino(N-methyl-4,2-pyrrole)carbonylimino)(3,5-naphthalendisulfonic acid);
6-(Amino-N-methyl-4,2-pyrrolecarbonyl-imino(N-methyl-4,2-pyrrole)carbonylimino)(3,5-naphthalendisulfonic acid);
8-(Amino-N-methyl-4,2-pyrrolecarbonyl-imino(N-methyl-4,2-pyrrole)carbonylimino)(3,6-naphthalendisulfonic acid);
7-(Amino-N-methyl-4,2-pyrrolecarbonyl-imino(N-methyl-4,2-pyrrole)carbonylimino)(3,6-naphthalendisulfonic acid);
8-(Amino-N-methyl-4,2-pyrrolecarbonyl-imino(N-methyl-4,2-pyrrole)carbonylimino)(1-naphthalensulfonic acid);
7-(Amino-N-methyl-4,2-pyrrolecarbonyl-imino(N-methyl-4,2-pyrrole)carbonylimino)(1-naphthalensulfonic acid);
8-(Amino-N-methyl-4,2-pyrrolecarbonyl-imino(N-methyl-4,2-pyrrole)carbonylimino)(3-naphthalensulfonic acid);
7-(Amino-N-methyl-4,2-pyrrolecarbonyl-imino(N-methyl-4,2-pyrrole)carbonylimino)(3-naphthalensulfonic acid);
8-(Amino-N-methyl-4,2-pyrrolecarbonyl-imino(N-methyl-4,2-pyrrole)carbonylimino)(5-naphthalensulfonic acid);
7-(Amino-N-methyl-4,2-pyrrolecarbonyl-imino(N-methyl-4,2-pyrrole)carbonylimino)(5-naphthalensulfonic acid);
8-(Amino-N-methyl-4,2-pyrrolecarbonyl-imino(N-methyl-4,2-pyrrole)carbonylimino(N-methyl-4,2-pyrrole)carbonylimino)(1,3,5-naphthalentrisulfonic acid);
7-(Amino-N-methyl-4,2-pyrrolecarbonyl-imino(N-methyl-4,2-pyrrole)carbonyl-imino(N-methyl-4,2-pyrrole)carbonylimino)(1,3,5-naphthalentrisulfonic acid);
6-(Amino-N-methyl-4,2-pyrrolecarbonyl-imino(N-methyl-4,2-pyrrole)carbonyl-imino(N-methyl-4,2-pyrrole)carbonylimino)(1,3,5-naphthalentrisulfonic acid);
8-(Amino-N-methyl-4,2-pyrrolecarbonyl-imino(N-methyl-4,2-pyrrole)carbonyl-imino(N-methyl-4,2-pyrrole)carbonylimino)(1,3,6-naphthalentrisulfonic acid);
7-(Amino-N-methyl-4,2-pyrrolecarbonyl-imino(N-methyl-4,2-pyrrole)carbonyl-imino(N-methyl-4,2-pyrrole) carbonylimino)(1,3,6-naphthalentrisulfonic acid);
8-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);
7-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);
6-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);
5-(Amino-N-methyl-4,2-pyrrolecarbonyl-imino(N-methyl-4,2-pyrrole)carbonyl-imino(N-methyl-4,2-pyrrole)carbonylimino)(1,3-naphthalendisulfonic acid);
8-(Amino-N-methyl-4,2-pyrrolecarbonyl-imino(N-methyl-4,2-pyrrole)carbonyl-imino(N-methyl-4,2-pyrrole)carbonylimino)(1,5-naphthalendisulfonic acid);
7-(Amino-N-methyl-4,2-pyrrolecarbonyl-imino(N-methyl-4,2-pyrrole)carbonyl-imino(N-methyl-4,2-pyrrole)carbonylimino)(1,5-naphthalendisulfonic acid);
6-(Amino-N-methyl-4,2-pyrrolecarbonyl-imino(N-methyl-4,2-pyrrole)carbonyl-imino(N-methyl-4,2-pyrrole)carbonylimino)(1,5-naphthalendisulfonic acid);
8-(Amino-N-methyl-4,2-pyrrolecarbonyl-imino(N-methyl-4,2-pyrrole)carbonyl-imino(N-methyl-4,2-pyrrole)carbonylimino)(3,5-naphthalendisulfonic acid);
7-(Amino-N-methyl-4,2-pyrrolecarbonyl-imino(N-methyl-4,2-pyrrole)carbonyl-imino(N-methyl-4,2-pyrrole)carbonylimino)(3,5-naphthalendisulfonic acid);
6-(Amino-N-methyl-4,2-pyrrolecarbonyl-imino(N-methyl-4,2-pyrrole)carbonyl-imino(N-methyl-4,2-pyrrole)carbonylimino)(3,5-naphthalendisulfonic acid);
8-(Amino-N-methyl-4,2-pyrrolecarbonyl-imino(N-methyl-4,2-pyrrole)carbonyl-imino(N-methyl- 4,2-pyrrole)carbonylimino)(3,6naphthalendisulfonic acid);
7-(Amino-N-methyl-4,2-pyrrolecarbonyl-imino(N-methyl-4,2-pyrrole)carbonyl-imino(N-methyl-4,2-pyrrole)carbonylimino)(3,6-naphthalendisulfonic acid);
8-(Amino-N-methyl-4,2-pyrrolecarbonyl-imino(N-methyl-4,2-pyrrole)carbonyl-imino(N-methyl-4,2-pyrrole)carbonylimino)(1-naphthalensulfonic acid);
7-(Amino-N-methyl-4,2-pyrrolecarbonyl-imino(N-methyl-4,2-pyrrole)carbonyl-imino(N-methyl-4,2-pyrrole)carbonylimino)(1naphthalensulfonic acid);
8-(Amino-N-methyl-4,2-pyrrolecarbonyl-imino(N-methyl-4,2-pyrrole)carbonyl-imino(N-methyl-4,2-pyrrole)carbonylimino)(3-naphthalensulfonic acid);
7-(Amino-N-methyl-4,2-pyrrolecarbonyl-imino(N-methyl-4,2-pyrrole)carbonyl-imino(N-methyl-4,2-pyrrole)carbonylimino)(3-naphthalensulfonic acid);
8-(Amino-N-methyl-4,2-pyrrolecarbonyl-imino(N-methyl-4,2-pyrrole)carbonyl-imino(N-methyl-4,2-pyrrole)carbonylimino)(5-naphthalensulfonic acid);

7-(Amino-N-methyl-4,2-pyrrolecarbonyl-imino(N-methyl-4,2-pyrrole)carbonyl-imino(N-methyl-4,2-pyrrole)carbonylimino)(5naphthalensulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3,5-naphthalentrisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3,5-naphthalentrisulfonic acid);

6-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3,5-naphthalentrisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3,6-naphthalentrisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3,6-naphthalentrisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3-naphthalendisulfonic acid);

6-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,3-naphthalendisulfonic acid);

5-(Amino-N-methyl-4,2-pyrrolecarbonyl-imino-(N-methyl-4,2-pyrrole(carbonyl-imino(N-methyl-4,2-pyrrole)carbonyl-imino(N-methyl-4,2-pyrrole)carbonylimino (1,3-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,5-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,5-naphthalendisulfonic acid);

6-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1,5-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,5-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,5-naphthalendisulfonic acid);

6-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,5-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,6-naphthalendisulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3,6-naphthalendisulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1-naphthalensulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (1-naphthalensulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3-naphthalensulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (3-naphthalensulfonic acid);

8-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (5-naphthalensulfonic acid);

7-(Amino-N-methyl-4,2-pyrrolecarbonyl-imino-(N-methyl-4,2-pyrrole)carbonyl-imino(N-methyl-4,2-pyrrole)carbonyl-imino(N-methyl-4,2-pyrrole)carbonylimino (5-naphthalensulfonic acid).

EXAMPLE 2

8-(Nitro-N-methyl-4,2-pyrrolecarbonyl-imino(N-methyl-4,2-pyrrole) carbonylimino))(1,3,5-naphthalentrisulfonic acid trisodium salt).

To a solution of 8-(amino(N-methyl-4,2-pyrrole) carbonyl imino) (1,3,5-naphthalentrisulfonic acid trisodium salt) hydrochloride (1.824 g, 3 mmols) in water (45 ml) and 1N NaOH (1 ml), sodium acetate (0.492 g, 6 mmols) was added under stirring.

The solution was cooled at 5° C. with an ice bath, then a solution of (4-nitro-N-methyl-2-pyrrole)carbonyl chloride (0.567 g, 3mmols) in dioxane (30 ml) was added dropwise in 1 h. The mixture was stirred 1 h at 5° C., acidified at pH 4 with 1N HCl and evaporated under vacuum to dryness. The residue was treated with ethyl acetate (300 ml), stirred for 1 hours and filtered, to obtain the title compound (2.1 g).

I.R. (KBr) cm$^{-1}$: 3440 b, 1650, 1520, 1305, 1195, 1030 N.M.R. (DMSO-d6; 80 M.Hz): 3.89 (3H,s); 3.99 (3H,s); 7.18 (1H,d); 7.46 (1H,d); 7.70 (1H,d); 8.02 (2H,m); 8.2 (1H,d); 8.63 (1H,d); 9.41 (1H,d); 10.45 (1H,b s); 12.42 (1H,b s);

EXAMPLE 3

8-(Amino(N-methyl-4,2-pyrrole)carbonylimino)(1,3,5-naphthalentrisulfonic acid trisodium salt), hydrochloride.

The solution of 8-(nitro(N-methyl-4,2-pyrrole)carbonylimino)(1,3,5-naphthalentrisulfonic acid trisodium salt) (1.803 g =3 mmols) in water (120 ml) and 1NHCl (3 ml) was reduced over a Pd catalyst (10% on carbon g 800) under $H_2$ pressure ( 50 p.s.i. ) for 4 h. The catalyst was filtered and the resulting solution was concentrated in vacuum to dryness, affording 1.8 g of the title compound.

I.R. (KBr) cm$^{-1}$: 3440 b, 1640, 1520, 1190, 1030 N.M.R. (DMSO-d6): 3.9 (3H,s); 7.11 (1H,d); 7.29 (1H,d); 8.04 (2H,m); 8.6 (1H,d); 9.88 (1H,d); 10.04 (3H,b s). 12.39 (1H,b s)

EXAMPLE 4

8-(Nitro(N-methyl-4,2-pyrrole)carbonylimino)(1,3,5-naphthalen trisulfonic acid trisodium salt. To a solution of 8-amino-1,3,5-naphthalentrisulfonic acid trisodium salt (1.347 g=3 mmols) in water (45 ml), sodium acetate (0.492 g=6mM) was added under stirring. The solution was cooled at 5° C. with an ice bath, then a solution of (4-nitro-N-methyl-2-pyrrole) carbonyl chloride (0.943=5 mmols) in dioxane (45 ml) was added dropwise in 1 h. The mixture was stirred 3 h at 5° C., acidified and pH 4 with 1N HCl and evaporated under vacuum to dryness. The residue was treated with ethylacetate (300 ml), stirred for 1 hour and filtered, to obtain g 1.7 of the title compound.

I.R. (KBr) cm$^{-1}$: 3440 b, 1650, 1530, 1305, 1200, 1030.
N.M.R. (DMSO-d6): 3.96 (3H,s); 7.84 (1H,d); 8.06 (2H,m); 8.15 (1H,d); 8.63 (1H,d); 9.4 (1H,d); 12.55 (1H,b s).

EXAMPLE 5

8-(Amino-N-methyl-4,2-pyrrolecarbonyl-imino(N-methyl-4,2-pyrrole) carbonylimino)(1,3,5-naphthalentrisulfonic acid).

A solution of 8- ( amino-N-methyl-4,2-pyrrolecarbonyl-imino (N- methyl-4,2-pyrrole ) carbonylimino ) ( 1,3,5-naphthalentrisulfonic acid)trisodium salt (400 mg) in water (10 ml), is chromatographed on an Amberlite 1R-120(H) column (20 ml), with water as eluent. The solution is evaporated to dryness in vacuum, affording 0.3 g of the title compound.

EXAMPLE 6

Tablets each weighing 150 g and containing 60 mg of the active substance can be manufactured by blending and compressing the following ingredients:

8-(Amino-N-methyl-4,2-pyrrolecarbonyl-imino(N-methyl-4,2-pyrrole)carbonylimino)) (1,3,5-naphthalentrisulfonic acid trisodium salt), hydrochloride 60 mg
Starch 50 mg
Cellule microcrystalline 30 mg
Polyvinylpyrrolidone 5 mg
Sodium carboxymethyl starch 4.5 mg
Magnesium stearate 0.5 mg

EXAMPLE 7

Capsules, each dosed at 200 mg and containing 80 mg of the active substance can be prepared as follows:

8-(Amino-N-methyl-4,2-pyrrolecarbonyl-imino(N-methyl-4,2-pyrrole)carbonylimino)) (1,3,5-naphthalentrisulfonic acid trisodium salt), hydrochloride 60 mg
Corn starch 60 mg
Cellulose microcrystalline 59 mg
Magnesium stearate 1 mg
This formulation can be encapsulated in two-piece hard gelatine capsules and dosed at 300 mg for each capsule.

EXAMPLE 8

Intramuscular injection 40 mg/ml
A injectable pharmaceutical preparation can be manufactured by dissolving 40 g of the active substance 8-(Amino-N-methyl-4,2-pyrrolecarbonyl-imino(N-methyl-4,2-pyrrole)carbonylimino))(1,3,5-naphthalentrisulfonic acid trisodium salt), hydrochloride in water for injection (1000 ml) and sealing ampoules of 1–10 ml.

We claim:

1. A pharmaceutical composition comprising a pharmaceutically acceptable carrier or diluent and, as an active principle, a naphthalenesulfonic-pyrrolecarboxamide derivative of formula (I)

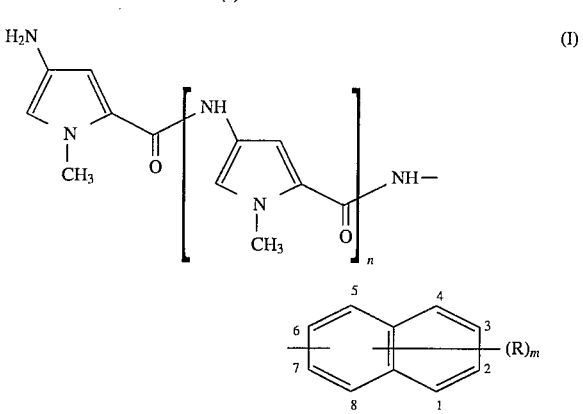

wherein n is zero or an integer of 1 to 3, R is a sulfonic acid residue and m is an integer of 1 to 3; or a pharmaceutically acceptable salt thereof.

2. A naphthalensulfonic-pyrrolecarboxamide derivative of formula (I):

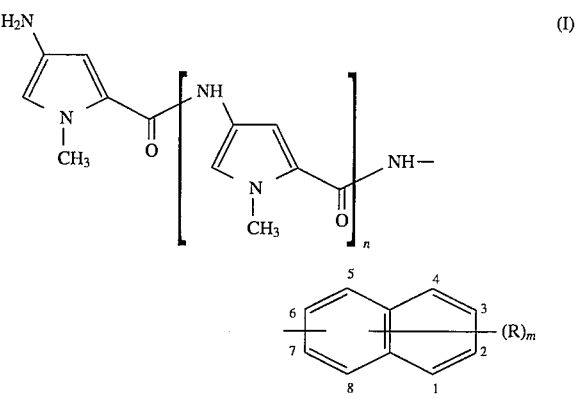

wherein n is 3, R is a sulfonic acid residue and m is an integer of 1 to 3; or a pharmaceutically acceptable salt thereof.

* * * * *